(12) United States Patent
Meulink et al.

(10) Patent No.: US 6,238,435 B1
(45) Date of Patent: May 29, 2001

(54) ASSEMBLY TOOL FOR PROSTHETIC IMPLANT

(75) Inventors: Steven Lee Meulink, Winona Lake; Stephen R. Rozow, III, Milford, both of IN (US)

(73) Assignee: Bristol-Myers Squibb Co, New York, NY (US)

( * ) Notice: Subject to any disclaimer, the term of this patent is extended or adjusted under 35 U.S.C. 154(b) by 0 days.

(21) Appl. No.: 09/523,545

(22) Filed: Mar. 10, 2000

(51) Int. Cl.$^7$ ....................................................... A61F 2/32
(52) U.S. Cl. .......................... 623/22.12; 606/85; 606/99; 606/100
(58) Field of Search ............................... 623/22.12, 22.11, 623/18.11, 908, 902; 606/86, 87, 88, 89, 90, 95, 96, 99, 100

(56) References Cited

U.S. PATENT DOCUMENTS

| 3,067,740 | 12/1962 | Haboush . | |
|---|---|---|---|
| 4,676,797 | 6/1987 | Anapliotis . | |
| 4,790,854 | 12/1988 | Harder . | |
| 4,878,917 | 11/1989 | Kranz . | |
| 5,190,550 | * 3/1993 | Miller et al. | 606/85 |
| 5,290,313 | 3/1994 | Heldreth . | |
| 5,913,860 | * 6/1999 | Scholl | 606/100 |
| 6,110,179 | * 8/2000 | Flivik et al. | 606/99 |
| 6,159,215 | * 12/2000 | Urbahns et al. | 606/86 |

OTHER PUBLICATIONS

William H. Harris, M.D., HG Multilock Hip Prosthesis, Surgical Technique for Primary Hip Arthroplasty 1990.
Biomet, Positively Impact Your Clinical Results 1992.
Cameron (Johnson & Johnson Orthopaedics), The S–Rom Total Hip System, Surgical Procedure 1994.
Link America, Inc., The Link MP Reconstruction Hip Stem Surgical 1997.
Kotz, Orthopadische Universitatsklinik, Kotz Modular Femur and Tibia Reconstruction System 1983.

* cited by examiner

*Primary Examiner*—Pedro Philogene
(74) *Attorney, Agent, or Firm*—Cary R. Reeves

(57) ABSTRACT

An instrument for seating taper junctions of modular implants engages two components and provides a sustained assembly force along the junction axis with great mechanical advantage. In one embodiment the instrument comprises a lever mechanism for generating the mechanical advantage. In another embodiment, the instrument provides for an indicator of the amount of force being applied to the junction. In another embodiment, the instrument engages the components for such that both assembly and disassembly can be accomplished.

17 Claims, 5 Drawing Sheets

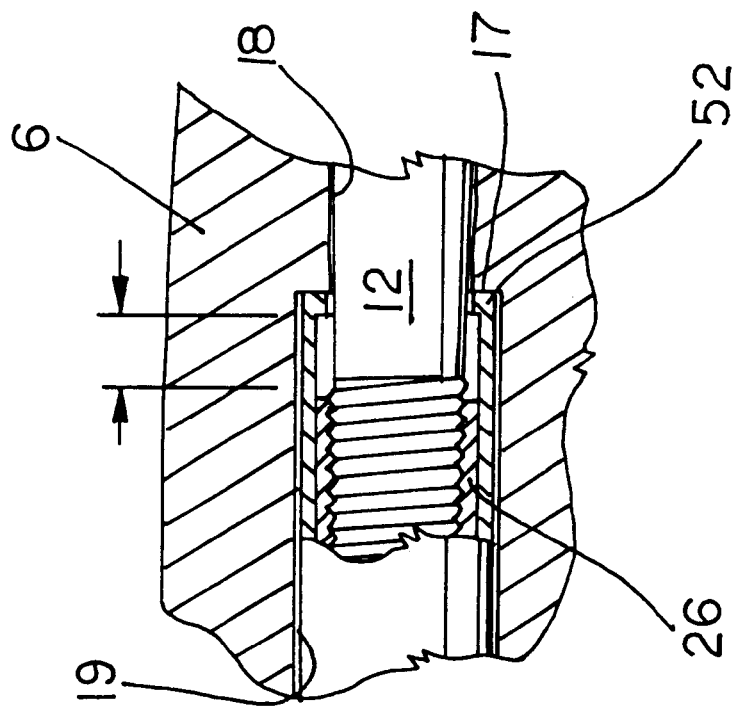
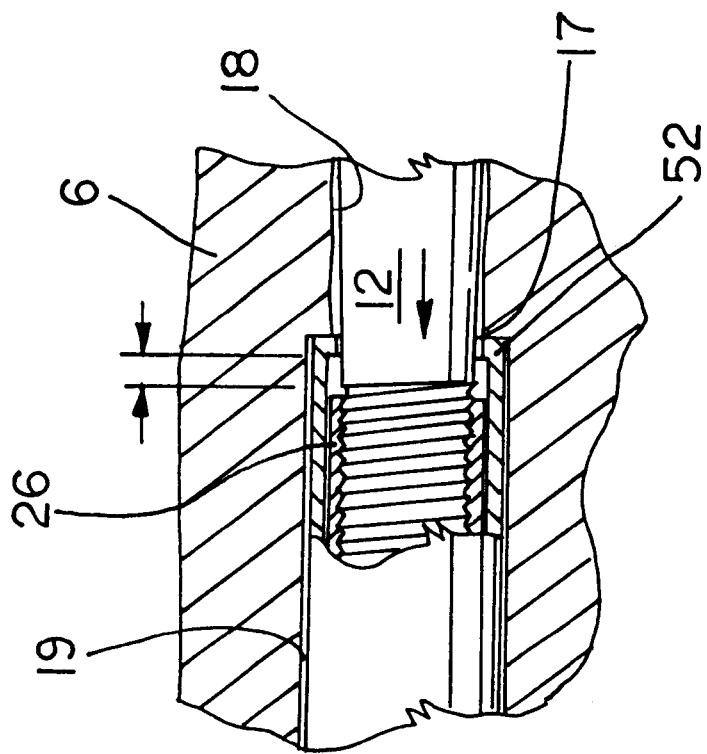

ASSEMBLY TOOL FOR PROSTHETIC IMPLANT

BACKGROUND OF THE INVENTION

The present invention relates to a tool for assembling a multicomponent prosthesis. More particularly, the present invention relates to a tool for compressing a taper junction between two components of an orthopaedic joint replacement component.

It is known in the art of orthopaedic joint replacement to provide an implant having multiple components that are assembled at the time of surgery. For example, it is known to provide a stemmed implant in which the stem is provided separately from a body portion. Typically, the junction between the components includes corresponding male and female tapers. An example of such an implant for hip replacement surgery is taught in U.S. Pat. No. 3,067,740. An example of such an implant for knee replacement surgery is taught in U.S. Pat. No. 5,290,313. Note that in this patent, the tapers are self-locking tapers. A screw (not shown) is described as optionally useful to further secure the junction against loosening. Other exemplary prior art taper junctions include hip femoral head-to-stem junction, shoulder humeral head-to-stem junction, knee femoral component-to-stem junction, segmental long bone component-to-component junction, and many others. In these prior art taper junctions, the junction is held with threaded fasteners, self-locking tapers, or a combination of threaded fasteners and self-locking tapers. It is important that the mating tapers be well seated for a tight assembly. In the case of self-locking tapers, it is known to impact the tapers together by using a mallet until they lock. Where threaded fasteners are used, it is taught, as in U.S. Pat. No. 3,067,740, to seat the taper junction by tightening the fastener. U.S. Pat. No. 5,290,313 teaches first seating the junction to lock the tapers and then applying the threaded fasteners.

SUMMARY OF THE INVENTION

The present invention improves on the use of taper junctions by providing an instrument for seating these junctions more consistently and with more force than is possible with impact techniques or the use of threaded implant fasteners.

The junction assembly instrument engages first and second components and provides a sustained assembly force along the junction axis with great mechanical advantage. In one embodiment the instrument comprises a lever mechanism for generating the mechanical advantage. In another embodiment, the instrument provides for an indicator of the amount of force being applied to the junction. In another embodiment, the instrument engages the components such that both assembly and disassembly can be accomplished.

BRIEF DESCRIPTION OF THE DRAWINGS

FIG. 4 is a partially sectioned detail view of the embodiment of FIG. 1 prior to compression of the implant junction.

FIG. 5 is a partially sectioned detail view of the embodiment of FIG. 1 after compression of the implant junction.

DETAILED DESCRIPTION OF THE INVENTION

Figure 1:
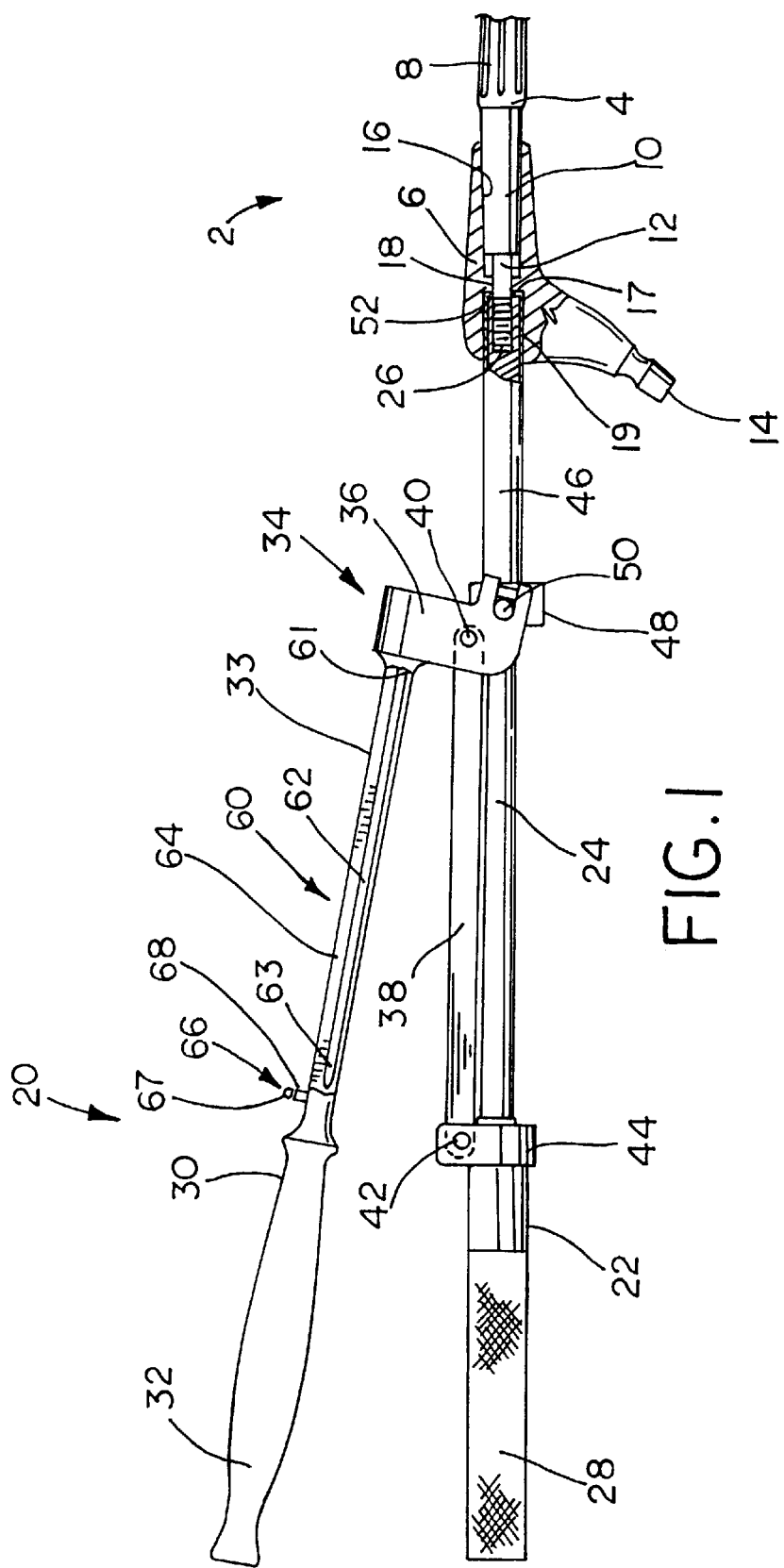
FIG. 1 is a partially sectioned frontal view of an embodiment of the present invention engaged with a modular hip stem prosthesis.
Figure 2:
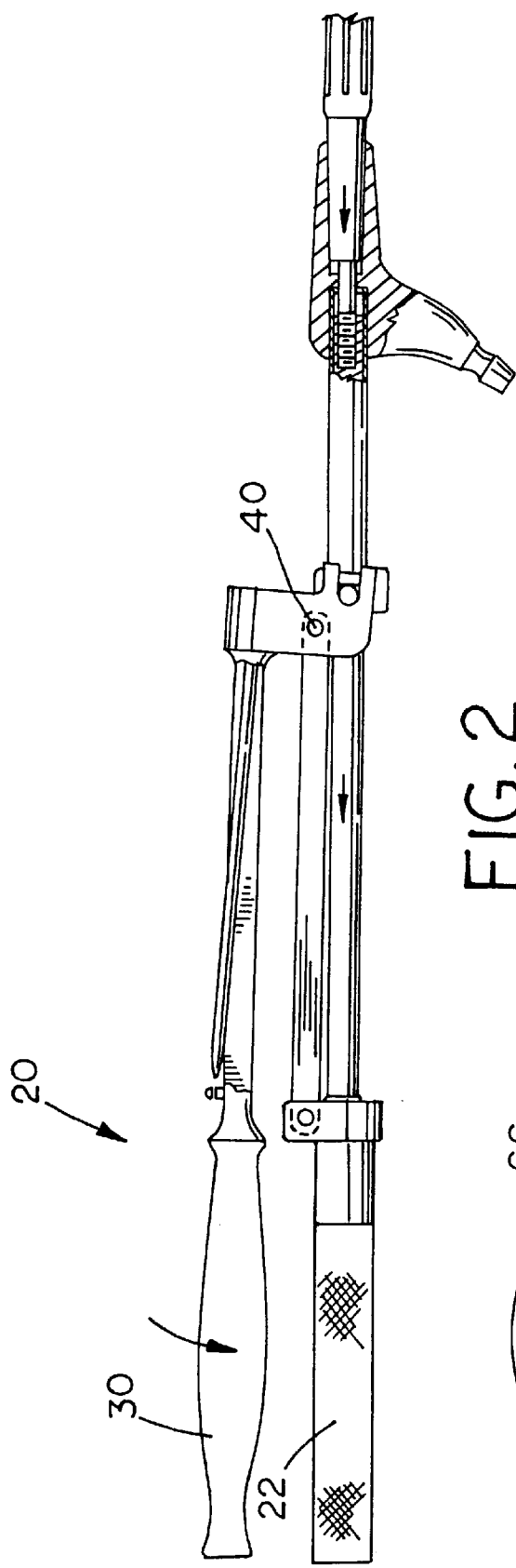
FIG. 2 is a partially sectioned frontal view of the embodiment of FIG. 1 with the operating handle moved to the compressed position.
Figure 3:
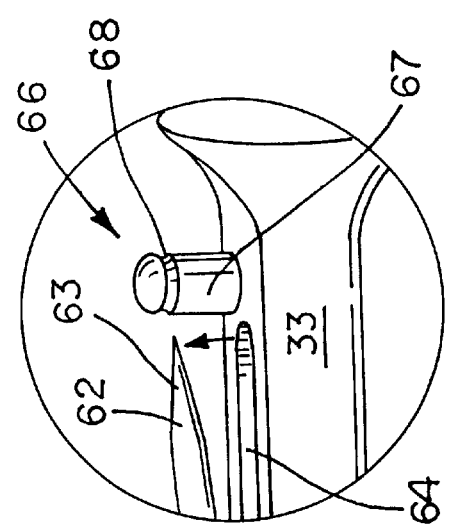
FIG. 3 is a detail view showing the operation of an indicator according to one embodiment of the invention.

FIGS. 1–7 depict an illustrative junction assembly instrument for assembling first and second joint components. This particular illustrative example is shown being adapted for compressing a self-locking taper junction between a stem component and a proximal body component of a modular hip stem.

A modular hip stem implant 2 includes a stem component 4 and a proximal body component 6. The stem component 4 has a bone contact portion 8 and a male taper junction portion 10. A threaded stud 12 extends from the male taper 10. The proximal body 6 includes a joint portion 14, a female taper 16, and a through hole 18 communicating with the female taper 16. The through hole 18 is axially aligned with the female taper 16. The through hole is preferably enlarged 19 proximally and includes a shoulder 17. The hip stem implant 2 is assembled by axially aligning and seating the male taper 10 within the female taper 16. Preferably the taper junction is self-locking such that upon being firmly seated the male and female tapers 10, 16 require great force to separate. The threaded stud 12 can be fitted with a nut (not shown) seated against shoulder 17 within enlarged opening 19 to further secure the junction.

A junction assembly tool 20 is advantageously used to seat modular components such as in the above described hip stem implant 2. The tool 20 includes stationary handle 22 having a shaft 24 terminating in an engagement end 26 and a grip end 28. The engagement end 26 is threaded for engaging the threaded stud 12 in axial force transmitting relationship. A pivot handle 30 includes a grip end 32, a shaft 33, and a working end 34. The working end includes an L-shaped pivot block 36. The pivot block 36 is connected to the stationary handle 22 via a connecting link 38 pinned at one end to the pivot block 36 to form a fulcrum 40 and pinned 42 at the other end to a mounting ring 44 affixed to the stationary handle 22. A second engagement member 46 is mounted adjacent engagement end 26 of stationary handle 22 and is movable relative to engagement end 26. In the exemplary embodiment, the second engagement member 46 is a sleeve coaxially mounted on engagement end 26 for longitudinal translation relative to engagement end 26. A first end 48 of the second engagement member 46 is linked to the pivot block 36 and thus to the working end 34 of the pivot handle 30 by a connecting pin 50. A second end 52 of the second engagement member 46 engages proximal body component 6 at shoulder 17 through enlarged portion 19 of through hole 18.

An indicator 60 includes a pointer 62 having a first end 61 attached to the pivot handle 30 near the working end 34 and a second end 63 cantilevered away from the working end 34. The pointed extends adjacent the pivot handle shaft 33. Preferably, the pivot handle shaft 33 includes a longitudinal channel 64 in which the pointer 62 is positioned. The pivot handle shaft 33 includes a scale 66 adjacent the second end 63 of the pointer 62. In the example, the scale 66 comprises a post 67 projecting from the shaft 33 and including an indicia mark 68.

FIGS. 2–7 illustrate the use of the junction assembly tool 20 to assemble the modular hip stem implant 2 of FIG. 1. Proximal body 6 is placed on stem 4 with the female taper 16 engaging the male taper 10 and threaded stud 12 extending through through hole 18. Engagement end 26 of stationary handle 22 is threaded onto threaded stud 12. If the handles 22,30 are held loosely, pivot handle 30 will swing away from stationary handle 22 as the second end 52 of second engagement member 46 presses against shoulder 17. This separation of the handles 22, 30 is a result of the second engagement member 46 moving back along the engagement end 26. As it moves back it pivots the pivot block 36 and thus the pivot handle 30 about the fulcrum 40. By connecting the pivot block via the elongate connecting link 38, the fulcrum 40 is permitted to move up and down slightly to prevent binding of the mechanism. Once the engagement end 26 securely engages the implant stem 4, the handles are brought together to seat the stem 4 and proximal body 6 components. Forcing the handles together moves second engagement member 46 outwardly relative to engagement end 26. The second end 52 presses against the proximal body 6 causing the proximal body 6 to move relative to the stem 4 into taper seating arrangement.

The coaxial arrangement of engagement member 46 and engagement end 26 is advantageous since it uniformly loads the tapers with a centrally aligned force through the threaded stud 12 and a uniform annular force against the shoulder 17.

Figure 6:
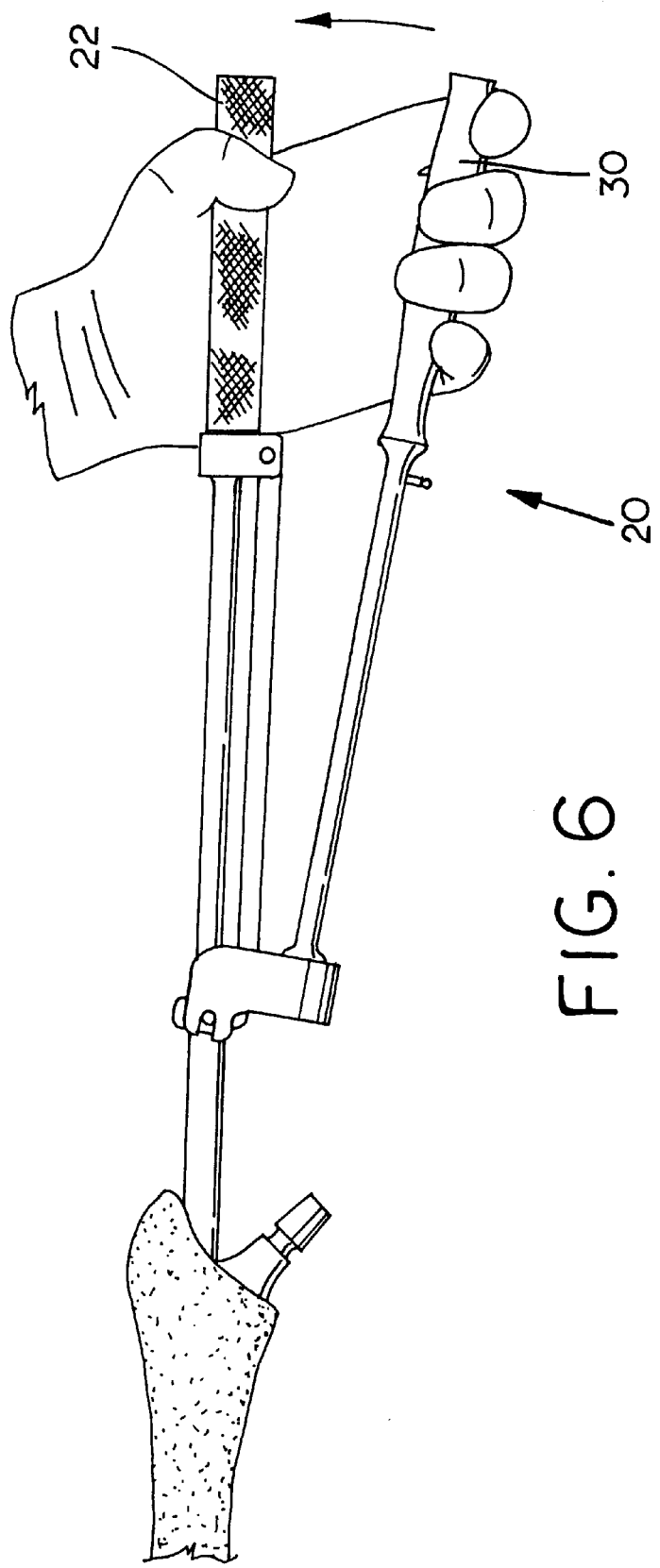
FIG. 6 is a frontal view of the embodiment of FIG. 1 shown in use to assemble a modular implant in vivo.
Figure 7:
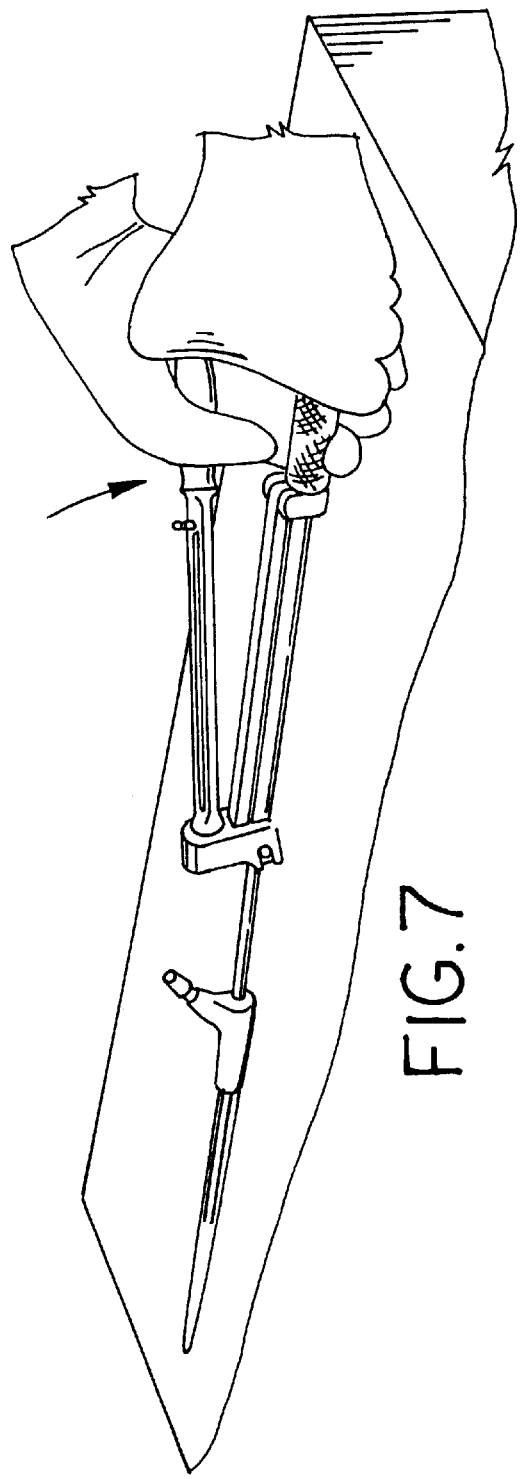
FIG. 7 is a frontal view of the embodiment of FIG. 1 shown in use to assemble a modular implant on an operating room table.

The axial arrangement of the handles in the illustrated embodiment is advantageous in that it allows for an elongate narrow tool. This configuration facilitates entry into narrow confines such as when the tool is used to seat implant components in-vivo as shown in FIG. 6. However, the configuration is still easily used for back table assembly in the operating room as shown in FIG. 7. In addition, the axial handle arrangement allows for large forces to be generated at the taper junction due to the relatively long distance from the grips 28,32 to the fulcrum 40 and the relatively short distance from the fulcrum 40 to the connecting pin 50. The axial arrangement further contributes to high force capacity since a two-handed grip can be employed to make use of the entire upper body strength of the user if necessary.

Force applied to the pivot handle 30 tends to flex the pivot handle shaft 33. Since the pointer 62 is cantilevered away from the working end 34, it does not flex with the pivot handle shaft 33. The amount of deflection of the pivot handle shaft 33 relative to the pointer 62 is a function of the amount of force applied to the handles and consequently is a function of the opposing forces applied to seat the tapers. By operating the handles to produce a predetermined relative deflection, a predetermined taper seating force be reproducibly applied. The scale 66 provides a convenient way to measure handle deflection. When the pointer 62 is aligned with the indicia mark 68 on the post 67 a predetermined force is applied to the taper junction. When the junction assembly tool is not in use, the pointer 62 is housed in the channel 64 which protects against damage to the pointer and its surroundings.

Figure 8:
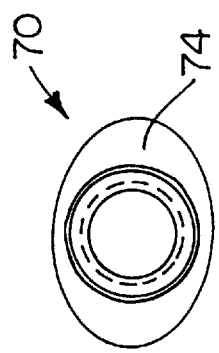
FIG. 8 is a bottom view of an alternative embodiment of an engagement end of the present invention.
Figure 9:
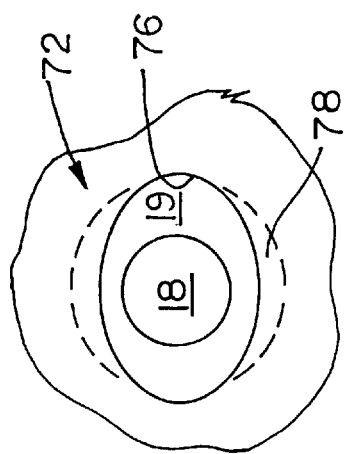
FIG. 9 is a top view of a mating implant component for use with the engagement end of FIG. 8.
Figure 10:
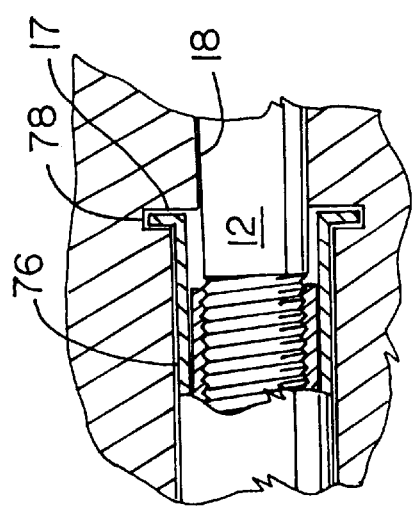
FIG. 10 is a side view of the engagement end of FIG. 8 received in the implant component of FIG. 9.

The exemplary embodiment has illustrated a tool for seating a junction between implant components. With only minor modification, the same tool can also be used for unseating the components. In the embodiment of FIGS. 1–7, the second end 52 of the second engagement member 46 presses against the proximal body 6 at shoulder 17 to seat the junction. If the handles are then moved apart, second end 52 retracts away from the shoulder. This is because although the threaded engagement between engagement end 26 and threaded stud 12 is capable of bi-directional force transmission, the pressing engagement of the second end 52 with the shoulder 17 is not bi-directional. If, on the other hand, second end 52 were bi-directionally engageable with proximal body 6, then moving the handles apart would cause the joint components to move out of taper seated arrangement. FIG. 8 illustrates an alternate exemplary engagement end 70 for second engagement member 46 capable of bi-directional force transmission. FIG. 9 illustrates an alternative configuration 72 for the enlarged opening 19 of the proximal body 6. The engagement end 70 has an oval tab 74 projecting radially from it. Enlarged opening 19 has a corresponding oval shaped side wall 76 for receiving the tab 74. An undercut slot 78 is formed in the side wall 76. The tab 74 can be axially inserted into the opening 19 and then rotated so that the tab engages the undercut slot for bi-directional force transmission as shown in FIG. 10.

It will be understood by those skilled in the art that many other variations in design and construction may be made to the preferred embodiment without departing from the spirit and scope of the invention defined by the appended claims.

What is claimed is:

1. A junction positioning tool for positioning a multiple component taper junction of a modular bone implant, the tool comprising:
   a longitudinal axis;
   a first member engaging a first component of the implant in axial first force transmitting relationship;
   a second member engaging a second component of the implant in axial second force transmitting relationship, the second force opposing the first; and
   a handle assembly engaging the first and second members, the handle assembly operative to move the first member relative to the second member along the axis to apply opposing forces to the first and second components.

2. The junction positioning tool of claim 1 wherein the handle assembly is operative to move the first and second components into taper seated arrangement.

3. The junction positioning tool of claim 2 further comprising an indicator attached to the tool, the indicator being responsive to operation of the handle assembly to indicate the amount of force being applied to the first and second components to move them into taper seated arrangement.

4. The junction positioning tool of claim 1 wherein the handle assembly is operative to move the first and second components out of taper seated arrangement.

5. The junction positioning tool of claim 1 wherein the first and second members each engage the first and second components for transmitting force both inwardly and outwardly along the axis such that the handle assembly is operative to move the first and second component both into and out of taper seated arrangement.

6. The junction positioning tool of claim 5 wherein one of the first and second members engages the corresponding implant component by way of a projecting boss axially rotatably engageable with an undercut slot.

7. The junction positioning tool of claim 1 wherein the handle assembly comprises a first handle and a second handle, the second handle being mounted for pivoting at a fulcrum relative to the first handle, pivoting of the second handle relative to the first handle being operative to move the first member relative to the second member along the axis.

8. The junction positioning tool of claim 7 wherein the first member comprises a shaft extending from the first handle and the second member comprises a sleeve coaxially mounted on the shaft for sliding along the shaft, the second handle being in force transmitting engagement with the sleeve, pivoting of the second handle relative to the first handle being operative to slide the sleeve along the axis.

9. The junction positioning tool of claim 8 wherein one of the first and second members threadably engages the corresponding implant component.

10. The junction positioning tool of claim 7 further comprising an indicator attached to the tool, the indicator being attached to the second handle near the fulcrum and extending from the fulcrum, deflection of the second handle relative to the indicator indicating the magnitude of the opposing forces applied to the first and second components.

11. The junction positioning tool of claim 10 further comprising a scale, the scale including at least one indicia mark, the scale being located on the second handle in spaced relation to the fulcrum, deflection of the second handle relative to the indicator moving the at least one indicia mark into alignment with the pointer at a predetermined magnitude of the opposing forces applied to the first and second components.

12. A junction assembly tool for seating a male taper of an implant stem component in a female taper of an implant body component wherein the stem component has a longitudinal axis and a screw thread formed near the narrow end of the male taper along the longitudinal axis and the body component has a through hole communicating with the narrow end of the female taper along the longitudinal axis, the tool comprising:

a stationary handle having a grip end, a shaft, and an engagement end, the engagement end threadably engageable with the screw thread of the stem component;

a pivot handle having a grip end and a working end, the working end being mounted for rotation about a fulcrum connected to the stationary handle;

a sleeve mounted coaxially on the stationary handle shaft for longitudinal translation relative to the engagement end, the sleeve having a first end linked to the working end of the pivot handle and a second end engageable with the body component, the pivot handle operable to force the sleeve in longintudinal translation along the shaft such that the engagement end of the stationary handle forces the screw thread in one direction along the longitudinal axis and the second end of the sleeve forces the body component in the opposite direction to move the male and female tapers into seating arrangement.

13. The junction assembly tool of claim 12 further including an indicator, the indicator including an elongate shaft having first and second ends, the shaft first end being mounted adjacent the working end of the pivot handle, the shaft second end being cantilevered away from the working end, deflection of the pivot handle relative to the indicator indicating the magnitude of the opposing forces applied to seat the male and female tapers.

14. The junction assembly tool of claim 13 wherein the pivot handle includes a longitudinal channel, the indicator shaft lying within the channel such that deflection of the pivot handle relative to the indicator shaft allows the second end of the indicator shaft to project out of the channel.

15. The junction assembly tool of claim 14 wherein the pivot handle includes a scale adjacent the second end of the indicator shaft, the scale including at least one indicia mark, the deflection of the pivot handle relative to the indicator shaft moving the at least one indicia mark into alignment with the second end of the indicator shaft at a predetermined magnitude of the opposing forces applied to the stem and body components.

16. The junction assembly tool of claim 12 wherein the stationary handle is in line with the longitudinal axis and the pivot handle is operable between a position in which it is aligned at a shallow angle with the longitudinal axis and a position in which it is aligned substantially parallel with the longitudinal axis such alignments facilitating a two-handed grip on the tool for applying large operational forces to the handles.

17. The junction assembly tool of claim 12 wherein the sleeve fits within a recess in the body component, the recess axially aligned with the through hole.

\* \* \* \* \*